US010251359B2

(12) United States Patent
Waycott

(10) Patent No.: US 10,251,359 B2
(45) Date of Patent: *Apr. 9, 2019

(54) TYPE OF LETTUCE AND METHODS OF PRODUCTION

(71) Applicant: Seminis Vegetable Seeds, Inc., St. Louis, MO (US)

(72) Inventor: William Waycott, San Luis Obispo, CA (US)

(73) Assignee: Seminis Vegetable Seeds, Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/018,930

(22) Filed: Jun. 26, 2018

(65) Prior Publication Data
US 2018/0303053 A1 Oct. 25, 2018

Related U.S. Application Data

(60) Continuation of application No. 15/200,566, filed on Jul. 1, 2016, now Pat. No. 10,021,849, which is a continuation of application No. 14/221,581, filed on Mar. 21, 2014, now Pat. No. 9,386,756, which is a continuation of application No. 13/336,422, filed on Dec. 23, 2011, now Pat. No. 8,729,343, which is a continuation of application No. 12/348,882, filed on Jan. 5, 2009, now Pat. No. 8,101,817, which is a continuation of application No. 10/665,029, filed on Sep. 16, 2003, now Pat. No. 7,563,952, which is a division of application No. 09/822,817, filed on Mar. 30, 2001, now Pat. No. 6,689,941.

(51) Int. Cl.
A01H 5/12 (2018.01)
A01H 6/14 (2018.01)

(52) U.S. Cl.
CPC .............. A01H 5/12 (2013.01); A01H 6/1472 (2018.05)

(58) Field of Classification Search
None
See application file for complete search history.

(56) References Cited

U.S. PATENT DOCUMENTS

| 3,800,518 | A | 4/1974 | Baggiolini et al. |
| 5,220,113 | A | 6/1993 | Miltz |
| 5,304,719 | A | 4/1994 | Segebart |
| 5,523,520 | A | 6/1996 | Hunsperger et al. |
| 5,763,755 | A | 6/1998 | Carlone |
| 5,850,009 | A | 12/1998 | Kevern |
| 5,973,232 | A | 10/1999 | Waycott et al. |
| 6,689,941 | B2 * | 2/2004 | Waycott ............... A01H 5/12 435/410 |
| 7,563,952 | B2 * | 7/2009 | Waycott ............... A01H 5/12 800/295 |
| 8,101,817 | B2 * | 1/2012 | Waycott ............... A01H 1/02 800/260 |
| 8,729,343 | B2 * | 5/2014 | Waycott ............... A01H 1/02 800/260 |
| 9,386,756 | B2 * | 7/2016 | Waycott ............... A01H 1/02 |
| 10,021,849 | B2 * | 7/2018 | Waycott ............... A01H 5/12 |
| 2005/0102718 | A1 | 5/2005 | Waycott |
| 2008/0184383 | A1 | 7/2008 | Waycott |
| 2009/0119802 | A1 | 5/2009 | Waycott |

FOREIGN PATENT DOCUMENTS

WO  WO 2002/078428 A2  10/2002
WO  WO 2008/091996 A2  7/2008

OTHER PUBLICATIONS

Bassett, "The Role of Leaf Shape in the Inheritance of Heading in Lettuce (*Lactuca sativa* L.)," *J. Amer. Soc. Hort. Sci.*, 100(2):104-105 (1975), in U.S. Appl. No. 10/665,029.

Bennetzen et al. "Approaches and Progress in the Molecular Cloning of Plant Disease Resistance Genes," *Genetic Engineering*, 14:99-124 (1992), in U.S. Appl. No. 10/665,029.

Campbell, "Lettuce Ring Necrosis, a Viruslike Disease of Lettuce: Evidence for Transmission by Olpidium brassicae," *Plant Disease* 80(6):611-615 (1996), in U.S. Appl. No. 12/348,882.

DeBolle et al. "Antimicrobial peptides from *Mirabilis Jalapa* and *Amaranthus caudatus*: expression, processing, localization and biological activity in transgenic tobacco," *Plant Molecular Biology*, 31:993-1008 (1996), in U.S. Appl. No. 10/665,029.

de Vries et al. "Numerical morphological analysis of Lettuce cultivars and species (*Lactuca* sect. *Lactuca, Asteraceae*)," *Plant Systematics and Evolution*, 193:125-141 (1994), in U.S. Appl. No. 10/665,029.

Doerge et al. "Nitrogen Fertilizer Management in Arizona," Pub. No. 191025, pp. 69-71 (1991) (available at http://ag.arizona.edu/crops/soils/nitfertmgt.html), in U.S. Appl. No. 12/348,882.

Eskins et al. "Light quality during early seedling development influences in the morphology and bitter taste intensity of mature lettuce (*Lactuca sativa*) leaves," *J. Plant Physiol.* 147:709-713 (1996), in U.S. Appl. No. 12/348,882.

Eshed et al. "Less-Than-Additive Epistatic Interactions of Quantitative Trait Loci in Tomato," *Genetics*, 143:1807-1817 (1996), in U.S. Appl. No. 10/665,029.

Guidelines for the Conduct of Tests for Distinctness, Homogeneity and Stability: Lettuce, International Union for the Protection of New Varieties of Plants, UPOVTG/12/7 (1993), in U.S. Appl. No. 12/348,882.

International Search Report, International Application No. PCT/US02/09345 (published as International Publication No. WO 02/078428 A3) (Aug. 5, 2003), in U.S. Appl. No. 12/348,882.

(Continued)

Primary Examiner — Eileen B O Hara
(74) Attorney, Agent, or Firm — Alissa M. Eagle; David R. Marsh; Arnold & Porter Kaye Scholer LLP

(57) ABSTRACT

The present invention relates to an iceberg lettuce having one or more romaine lettuce characteristics. The invention further relates to methods for producing iceberg lettuce varieties containing one or more romaine lettuce characteristics.

30 Claims, No Drawings

(56) References Cited

OTHER PUBLICATIONS

International Search Report, International Application No. PCT/US08/51903 (published as International Publication No. WO 2008/091996 A3) (Aug. 13, 2008), in U.S. Appl. No. 12/348,882.
Ke et al. "Leafy Head Formation of the Progenies of Transgenic Plants of Chinese Cabbage with Exogenous Auxin Genes," *Cell Research* 10:151-160 (2000).
Kerns et al. "Guidelines for head Lettuce Production in Arizona," IPM Series No. 12, pub No. az1099, Cooperative Extension, College of Agriculture and Life Sciences, University of Arizona, Tucson, Arizona, url:http://cals.Arizona.edu/crops.vegetables/cropmgt/az1099.html (1999), in U.S. Appl. No. 12/348,882.
Kraft et al. "Linkage disequilibrium and fingerprinting in sugar beet," *Theoretical Applied Genetics*, 101:323-326 (2000), in U.S. Appl. No. 10/665,029.
Langton et al. "Heterosis in crisphead lettuce (*Lactuca sativa* L.) hybrids," *Euphytica*, 49(1): 15-23 (1990), in U.S. Appl. No. 13/336,422.
Lewis, "Inheritance of Heading Characteristics in Lettuce Varieties," *Proceedings of the American Society for Horticultural Science*, 27$^t$ Ann. Meeting, Cleveland, OH, pp. 347-351 (1930), in U.S. Appl. No. 12/348,882.
Pang et al. "Expression of a gene encoding a scorpion insectotoxin peptide in yeast, bacteria and plants," *Gene*, 116:165-172 (1992) in U.S. Appl. No. 10/665,029.
Plant Breeder's Rights Application No. 08-6335 for Lettuce Variety *Lactuca sativa* L. PS 065106090, Canadian Food Inspection Agency, dated May 14, 2009, in U.S. Appl. No. 12/348,882.
Plant Breeder's Rights Crop Report and Variety Description for Lettuce Variety *Lactuca sativa* L. PS 6545691, Canadian Food Inspection Agency, Aug. 11, 2004, issued under Certificate No. 3455, dated Feb. 27, 2009, in U.S. Appl. No. 12/348,882.
Plant Breeder's Rights Crop Report and Variety Description for Lettuce Variety *Lactuca sativa* L. PS 6545701, Canadian Food Inspection Agency, dated May 26, 2004, in U.S. Appl. No. 12/348,882.
Plant Breeder's Rights Variety Description for Lettuce Variety *Lactuca sativa* L. PS 6545691, Commonwealth of Australia, issued under Certificate No. 3498, dated Mar. 27, 2008, in U.S. Appl. No. 12/348,882.
Plant Breeder's Rights Variety Description for Lettuce Variety *Lactuca sativa* L. PS 6545701, Commonwealth of Australia, issued under Certificate No. 3499, dated Mar. 27, 2008, in U.S. Appl. No. 12/348,882.
PVP Certificate No. 200000266 for Lettuce Variety *Lactuca sativa* L. PS 6545691, dated Apr. 19, 2005, in U.S. Appl. No. 12/348,882.
PVP Certificate No. 200400253 for Lettuce Variety *Lactuca sativa* L. PS 6545701, dated May 3, 2007, in U.S. Appl. No. 12/348,882.
PVP Certificate No. 200700126 for Lettuce Variety *Lactuca sativa* L. PS 06516090, dated Feb. 13, 2007, in U.S. Appl. No. 12/348,882.
Ryder, "Lettuce Genetics: Inheritance, Linkage, and Epistasis," *J. Amer. Soc. Hort. Sci*, 117(3):504-507 (1992), in U.S. Appl. No. 12/348,882.
Sequeira et al. "Resistance to corky root rot in lettuce," *Plant Disease Report*, 54(9):754-758 (1970), in U.S. Appl. No. 10/665,029.
Tillge, "Variety identification in *Lactuca sativa* L.," *Seed Sci. & Technol.*, 12:919-933 (1984), in U.S. Appl. No. 10/665,029.
Wareing et al. "Fungal Pathogens in Rotted Basal Leaves of lettuce in Humberside and Lancashire with Particular Reference to *Rhizoctonia solani*," *Plant Pathology*, 35:390-395 (1986) in U.S. Appl. No. 12/348,882.
Waycott et al. "Differentiation of nearly identical germplasm accessions by a combination of molecular and morphologic analyses," *Genome*, 37(4):577-583 (1994), in U.S. Appl. No. 10/65,029.
Wurr et al. "The influence of solar radiation and temperature on the head weight of crisp lettuce," *Journal of Horticultural Science* 66(2):183-190 (1991), in U.S. Appl. No. 12/348,882.
Xinrun et al. "Genotypic effects on tissue culture response of lettuce cotyledons," *J. Genet. & Breed.*, 46:287-290 (1992), in U.S. Appl. No. 10/665,029.

\* cited by examiner

TYPE OF LETTUCE AND METHODS OF PRODUCTION

CROSS-REFERENCE TO RELATED APPLICATIONS

This application is a continuation application of U.S. application Ser. No. 15/200,566, filed on Jul. 1, 2016, allowed, which is a continuation application of U.S. application Ser. No. 14/221,581, filed on Mar. 21, 2014, now U.S. Pat. No. 9,386,756, which is a continuation application of U.S. application Ser. No. 13/336,422, filed on Dec. 23, 2011, now U.S. Pat. No. 8,729,343, which is a continuation application of U.S. application Ser. No. 12/348,882, filed on Jan. 5, 2009, now U.S. Pat. No. 8,101,817, which is a continuation of U.S. application Ser. No. 10/665,029, filed on Sep. 16, 2003, now U.S. Pat. No. 7,563,952, which is a divisional of U.S. patent application Ser. No. 09/822,817, filed Mar. 30, 2001, now U.S. Pat. No. 6,689,941, all of which are incorporated herein by reference in their entireties.

FIELD OF INVENTION

The present invention relates to the field of plant breeding. More particularly, the present invention describes a lettuce plant type having the general shape of a romaine lettuce and having other qualities similar to iceberg lettuce. This new iceberg lettuce plant type has an elliptical plant shape, and spatulate shaped leaves generally recognizable in stature and appearance similar to romaine lettuce, instead of the normal spherical shaped plants with obovate shaped leaves of the iceberg. Other qualities of these plants, e.g., head weight, interior and exterior color, texture, density, and taste, are similar to iceberg lettuce.

BACKGROUND OF THE INVENTION

Lettuce, *Lactuca sativa* L., is a commercially important fresh leaf crop belonging to the Cichoreae tribe of the aster family (Asteraceae) which includes such other important crops as sunflowers and artichokes. Lettuce is widely grown throughout the temperate and subtropical regions of the world and is used predominantly as a fresh green in the human diet.

There are six morphological types of lettuce: iceberg (crisphead), romaine (cos), butterhead, leaf, stem and Latin. Ryder, E. J., 1979, *Leafy Salad Vegetables*, AVI Publishing Company. These basic lettuce types frequently form the basis for grouping lettuces as is commonly seen in supermarkets, grocery and produce stores.

The crisphead type is the most common in the United States, while butterheads and romaines are the popular types in northern and southern Europe. Id. In the United States, California is the leading producer of lettuce. California produces crisphead, leaf and romaine lettuce. In 1995, California's cash receipts for crisphead lettuce amounted to about $987 million dollars. 1996 California Agricultural Resource Directory. Furthermore, also in 1995, California exported about $154 million dollars of crisphead lettuce to other countries such as Japan, Canada, the European Union and Korea. Id.

Terms used herein to describe plants are explained in "Guidelines for the Conduct of Tests for Distinctness, Homogeneity and Stability" UPOV Ref. No. TG/13/7, 16 Oct. 1993, which is hereby incorporated by reference.

The iceberg group lettuces are characterized by their relatively large, spherical, dense heads averaging 20.0 cm in diameter and 1000 g in weight, which are borne on a set of frame leaves that form the base of the plant. The heads are composed of leaves that are spirally arranged on a stem with greatly foreshortened internodes, are tightly clasping upon one another forming a sphere of broadly shaped (obovate) leaves, where the length and width of each leaf is nearly identical, having length to width ratio (L/W ratio) of 1.0 approximates 20.0 cm in length to 20.0 in width. The length to width ratio for commercial iceberg lettuce varieties ranges from about 0.5 to 1.0. Outer leaves range in color intensity from dark green (Royal Horticultural Society Color Chart 146A) to green (RHS 146B) with inner leaves ranging from very pale green (RHS 145C) to white or blanched (RHS 145D). Iceberg lettuces have a closed head formation. Iceberg leaves have a high content of water—hence the name, "crisphead." More information regarding the general characteristics of iceberg lettuce may be found in Ryder, E. J., *Leafy Salad Vegetables*, AVI Publishing Company, which is hereby incorporated by reference.

The romaine group of lettuces are characterized by large, cylindrical, semi-firm heads averaging 30.0 cm in diameter and 800 g in weight, which are borne on a set of frame leaves that form the base of the plant. The heads are composed of leaves that are spirally arranged on a stem with greatly foreshortened internodes, are loosely clasping upon one another forming a roll of elongated, spatula-shaped (spatulate) leaves, where the length is normally 50% longer than the width, having a range of length to width ratios of 1.2 to 2.5, where 1.5 is most common. Romaine lettuces generally have a semi-open head formation. The name "romaine" comes from the French for "Roman". Outer leaves range in color intensity from dark green (RHS 146A) to mid-green (RHS 146B) to light green (RHS 146C) with inner leaves ranging from green (RHS 146B) to light green (RHS 146D). More information regarding the general characteristics of romaine lettuce may be found in Ryder, E. J., *Leafy Salad Vegetables*, AVI Publishing Company.

A major disadvantage of existing iceberg varieties lies in their shape. While they are widely used in salads and sandwiches for their unique taste and crunchy texture, the iceberg's round shape makes it difficult to process, resulting in inefficient handling and waste. For example, the iceberg lettuce head cannot be used when separating individual leaves to allow for cleaning and the production of individual lettuce leaves. The deeply cup-shaped leaves make thorough cleaning difficult and this same shape prevents their use as individual leaves in sandwiches because of their inability to lie flat and thus they are broken and damaged. In contrast, such disadvantages are not present in the shape of romaine lettuces.

Another disadvantage of existing iceberg varieties lies in their growing pattern. Because they grow low to the ground, harvesting must be done by hand. This means high harvest costs due to hand labor, which can also cause potential damage to the head when the lettuce stem is not cut at the correct level. Improperly harvested heads cannot be salvaged and must be discarded. In contrast, romaine lettuces grow erect and their leaves are oriented nearly vertically, thereby allowing for better access to the stem. These erect plants (such as a romaine) make the prospect of machine harvesting possible. Machine harvesting results in significant time and money savings.

Another disadvantage of existing iceberg varieties lies in their susceptibility to certain debilitating diseases. All plants rely on evaporation of moisture from the surface of their leaves to draw vital water and nutrients up into the remote areas where growth occurs. Due to the round head shape for crisphead lettuce, inner leaves are not exposed to light and air, thereby inhibiting evaporation of moisture from its inner leaves and the translocation of critically needed water, nutrients, and defensive agents to all interior areas of the head. Under these circumstances, the lack of calcium and other minerals in the process of leaf formation is a common problem in iceberg lettuce, causing brown and black spots (tipburn) to occur leading to the likelihood of subsequent infection by secondary pathogens such as bacteria and fungi, that result in the rapid decay and spoilage of the head from the inside out. In contrast, such diseases are much rarer in romaine lettuces due to the erect, semi-open shape of the head.

Other problems with existing cultivars adapted to western conditions include a lack of resistance to corky root rot and lettuce mosaic virus. Corky root rot is believed to be caused by a pathogenic soil bacterium of the genus *Rhizomonas*. One species of *Rhizomonas* that is commonly found to cause corky root rot is *R. suberifaciens*. Corky root rot accounts for significant lettuce crop loss in the western United States, particularly in the valleys of the central coast of California, i.e., the Salinas, Santa Maria, and Lompoc valleys.

Lettuce mosaic virus, on the other hand, is commonly found throughout the world, and occurs in all lettuce production areas of the United States. Vectored by the Green Peach aphid (*Myzus persicae*), outbreaks of lettuce mosaic virus can devastate an entire field within a short period of time.

Corky root rot symptoms include yellow bands on tap and lateral roots of lettuce seedlings. *Guide to Leafy Vegetable Production in the Far West*, Ron Smith, ed., California-Arizona Farm Press (1997). Yellow areas gradually expand and develop a green-brown color with cracks and rough areas on the root surface. The entire taproot may become brown, severely cracked and may cease to function. Feeder root systems are reduced and damaged. Roots become very brittle and break off easily. When the root is severely discolored, aboveground symptoms show up as wilting during warm temperatures, stunting and general poor, uneven growth. Loss of the root system results in stunted plants that are chlorotic and too small to harvest.

Lettuce mosaic virus symptoms first appear as vein clearing in the newly developed leaves followed by mottling (a mosaic appearance) and recurving of the leaves as they mature. Ryder, E. J., *Leafy Salad Vegetables*, AVI Publishing Company. The leaf margins increase in undulation and necrotic spots may also appear. Infected plants are generally much smaller than healthy plants, rendering the plants unsuitable for harvest.

SUMMARY OF THE INVENTION

The present invention relates to a new type of lettuce which combines a number of advantageous characteristics of romaine, e.g., a flat leaf shape, stature and semi-open headedness plus iceberg lettuce characteristics, e.g., large, spherical, firm heads with inner blanched leaves and a crunchy, bland texture.

The present invention relates to an iceberg lettuce plant having a first outer leaf having a length to width ratio of between about 1.2 and about 2.7. The present invention further relates to iceberg lettuce plants having spatulate leaf shape or an elliptical stature or a semi-open head formation. This invention is also directed to methods of producing an iceberg lettuce with a first outer leaf having a length to width ratio of between about 1.2 and about 2.7.

DETAILED DESCRIPTION OF THE INVENTION

Definitions—In the description and tables which follow, a number of terms are used. In order to provide a clear and consistent understanding of the specification and claims, including the scope to be given such terms, the following definitions are provided:

First outer leaf—As described herein, "first outer leaf" means the first leaf located on the outer surface of the lettuce head.

Leaf Length to Width Ratio (L/W Ratio)—As used herein, the length to width ratio is calculated by dividing the length of the first outer leaf by the width of the first outer leaf measured at the widest point.

Outer leaf—As used herein, the term "outer leaf" refers to the 10 outermost leaves on a head of lettuce.

Inner leaf—As used herein, the term "inner leaf" refers to the 10 leaves closest to the core of a head of lettuce.

This invention provides a new type of iceberg lettuce having a plant and leaf shape and stature similar to romaine lettuce. At maturity, the heads of the plants of the present invention generally measure more than 20.0 cm in length and are similar to a typical romaine plant height, whereas normal iceberg heads rarely exceed 20.0 cm.

A common problem in the creation of new varieties is the very low occurrence of the desired genetic phenotype in a large genetic population. With more than 10,000 genes known to exist in plants, it is often highly improbable, if not impossible to converge on all the desired genetic traits in one individual. Prior to this work, it was not known whether the modified shape and stature of romaine could be incorporated into a commercially viable iceberg lettuce variety. Previous work with iceberg x romaine combinations was not able to detect the unique genetic concurrence of stature and internal quality of the present invention.

Another common problem that may occur includes gene interactions, whereby the products of the genes interact. Such interaction may prevent the expression of a selected desirable trait. One form of gene interaction is epistasis, whereby interaction between products of non-allelic genes results in modification or masking of the desired phenotype. Epistasis may be brought about by modification of gene function due to alterations in the signal-transducing pathway. Epistasis may also occur indirectly through non-intracellular phenomena. For example, a plant with certain metabolites may exert deleterious effects on a developing embryo which does not normally produce such metabolites.

Another problem in the creation of new varieties includes linkage drag, whereby undesirable genes are brought into a population on the basis of hitchhiking if no recombination occurs between the selected desirable and undesirable genes.

In one aspect of the invention, methods for developing novel plant types are presented. In one preferred embodiment the specific type of breeding method is pedigree selection, where both single plant selection and mass selection practices are employed. Pedigree selection, also known as the "Vilmorin system of selection," is described in Fehr, Walter; *Principles of Cultivar Development*, Volume I, Macmillan Publishing Co., which is hereby incorporated by reference.

In general, selection is first practiced among $F_2$ plants. In the next season, the most desirable $F_3$ lines are first identified, then desirable $F_3$ plants within each line are selected.

The following season and in all subsequent generations of inbreeding, the most desirable families are identified first, then desirable lines within the selected families are chosen, and finally desirable plants within selected lines are harvested individually. A family refers to lines that were derived from plants selected from the same progeny row the preceding generation.

Using this pedigree method, two parents may be crossed using an emasculated female and a pollen donor (male) to produce $F_1$ offspring. To optimize crossing, it is important to note that lettuce is an obligate self-pollinating species. This means that the pollen is shed before stigma emergence, assuring 100% self-fertilization. Since each lettuce flower is an aggregate of about 10-20 individual florets, manual removal of the anther tubes containing the pollen is tedious. As such, a method of misting to wash the pollen off prior to fertilization may be employed to assure crossing or hybridization.

Any varieties of iceberg or romaine lettuce may be used as parents in the method of the present invention. More preferably, the parental varieties are selected from commercial varieties that individually exhibit one or more desired phenotypes. Also any breeding method involving selection of plants for the desired phenotype can be used in the method of the present invention.

The $F_1$ may be self-pollinated to produce a segregating $F_2$ generation. Individual plants may then be selected which represent the desired phenotype in each generation ($F_3$, $F_4$, $F_5$, etc.) until the traits are homozygous or fixed within a breeding population.

Although a number of different selection criteria may be used, the selection criteria may include one or more of the following:
1. identification of an iceberg cultivar with the shape and stature of a romaine lettuce
2. a semi-open head
3. dark outer color with blanched inner color
4. resistance to corky root rot
5. resistance to lettuce mosaic virus
6. length to width ratio of greater than 1.0, and
7. plant height.

The pathogen responsible for corky root is *Rhizomas suberifaciens*. CA1 is the most common strain and is publicly available from the ATCC (Accession No. 49355). Other useful strains include CA3 and CA15. Colonies of *R. suberifaciens* are initially translucent but later become opaque. The colonies are umbonate, compact colonies, which ultimately become wrinkled and have raised edges on S-medium as described in Van Bruggen, et al. 1990, Host Range of *Rhizomas suberifaciens*, the causal agent of corky root of lettuce, Plant Disease, 74:581-584.

*R. suberifaciens* is an aerobic bacterium, ranging in morphology from small (0.6-1.4 mu by 0.3-0.6 mu) rods with one lateral flagellum to long filaments. According to the KOH stringiness test, the bacteria seemed gram-positive, but with Hucker's gram-stain the bacteria stain was gram-negative.

The type CA1 and other equivalent strains are publicly available in the Salinas Valley of California growing in the soil of the lettuce fields. These strains are quite common and can be isolated using the baiting procedure described in Example 5. Characterized strains are also available from Dr. Ariena Van Bruggen at the University of California at Davis.

An initial screen for corky root is initiated using the screening procedure of Example 5. The seeds are sown under greenhouse-controlled conditions in vermiculite soil with a heavy concentration (approx. $10^7$ cfu/ml) of corky root bacteria. Susceptibility is determined by visually inspecting the tap roots for greenish-yellow to gold oblong lesions. Advanced symptoms include a greenish-brown to golden root system and a corky and brown taproot.

The major pathogenic race or pathotype of corky root is CA1, but other strains are known. The cor gene is recognized as a gene responsible for resistance.

Lettuce Mosaic Virus (LMV) is a potyvirus. Natural transmission of LMV is achieved by the green peach aphid (*Myzus persicae*) feeding on infected host leaves. Wild lettuce and bristly ox-tongue are the two most important natural hosts. The virus is non-persistent in the aphid and seed-borne. The common strain is available from the ATCC. The ATCC accession number is PV-63. Infected leaf tissue can be conveniently stored in a freezer at −20° Celsius.

Individual plants are inoculated with LMV as described in Example 6. The virus in ground leaves infected with LMV is mixed with a buffered solution and abraded with carborundum or sand onto the leaf surfaces of the test plants. Inoculation with LMV is at stand establishment when the plants have recovered from transplant shock. Stand establishment is about 3-4 weeks after transplanting, when the plants present two or three expanded leaves. Waiting until stand establishment increases the efficiency of screening for viral-induced mosaic symptoms.

Resistance to LMV is considered under the control of a single recessive gene. Resistant varieties are publicly available as described in Example 6 and can be used as starting material for introducing LMV into the present invention.

The development of all the lines discussed herein (PSR 4569, PSR 6425, PSR 6595, and PSR 6032) used similar selection techniques, although the parental combinations used to make each of the crosses were different. The main factor uniting these combinations of the present invention is the unique phenotype. This invention was facilitated by the selection criteria used in the breeding of these lines where the combination of a romaine shape and stature was linked to other qualities of an iceberg lettuce.

During the breeding and selection of the lines disclosed herein, there was no anticipated phenotype (expected biological design) due to the lack of prior work in this area of lettuce research and breeding. Once an acceptable phenotype had been identified, it became clear that the same desired characteristics could be obtained from a number of different parental combinations. However, this could only be done when the appropriate selection criteria were applied. Thus, only by making repeated selections for the desired phenotype could this invention be repeatedly produced.

The leaf shape of the present invention is spatulate. The term "spatulate" as used in this patent application includes leaf shapes varying from narrow elliptic or oblong to oblanceolate or broad obtrullate as described in TG/13/7, page 19 supra.

The stature of the present invention is elliptical. The term "elliptical" as used in this patent application includes statures varying from narrowly elliptical to broadly elliptical as described in TG/13/7, page 18 supra.

The length to width ratio of the outer leaf of the present invention is approximately 1.2 to 2.1. However, other embodiments of the invention can comprise ratios varying from about 1.2 to about 2.7. Preferably, the length to width ratio can vary from 1.25 to 2.2, most preferably 1.3 to 2.0.

Using Royal Horticultural Society's Color Chart the outer leaf color of the present invention is normally green (RHS 146B). However, other embodiments of the invention can comprise outer leaf colors varying from dark green (RHS 146A) to green (RHS 146B).

The lettuces of the present invention may have a semi-open head formation. The term "semi-open" as used in this patent application includes head formations varying from medium to strong as described in TG/13/7, page 13, heading 9 supra.

Although the forgoing invention has been described and illustrated, it should be understood that certain changes and modifications may be practiced within the scope of this invention without departing from the scope of the invention as set forth in the accompanying claims.

EXAMPLES

Example 1

Development and Characteristics of Lettuce Cultivar PSR 4569

PSR 4569 originated in 1993 with the cross of the romaine PI 206964 by cultivar Salinas 88; PI 206964 was obtained from the USDA's Western Regional Plant Introduction Station, Pullman, Wash. and Salinas 88 is a public variety released by the USDA in 1978. Single plant selections were made in subsequent years in the area of intended commercialization. By $F_6$, a group of 15 families was judged uniform and bulked for trialing and seed increase.

In 1993, the romaine variety PI 206964 which is an exotic plant introduction (PI), was crossed as the female parent with the crisphead lettuce cultivar Salinas 88 as the male parent using traditional cross hybridization techniques. PI 206964 is a romaine lettuce known to be a source of resistance to corky root rot and was obtained from the USDA's Western Regional Plant Introduction Station, Pullman, Wash. Salinas 88 is a public variety released by the USDA in 1978; it is a crisphead lettuce known to be a source of resistance to lettuce mosaic virus and was obtained from the United States Department of Agriculture, ARS, 1636 East Alisal Street, Salinas, Calif. 93905. The cross between the exotic romaine parent PI 206964 and Salinas 88 resulted in an unexpected new combination of characteristics, wherein an iceberg lettuce type had a taller plant stature, a larger length to width ratio plus other romaine lettuce characteristics.

This new combination of traits was derived from the breeding and selection techniques of the present invention. Using these techniques, a plant breeder can use any iceberg lettuce and any romaine lettuce with the method of the present invention to develop new varieties of iceberg lettuce having a first outer leaf with a length to width ratio of more than 1.0 and other romaine characteristics.

In 1994, the resulting $F_1$ seed from the cross was collected, planted, and allowed to self-pollinate. The resulting $F_2$ seed was collected. In 1995, the $F_2$ seed was planted. From the resulting plants, five plants were selected. The selection criteria for these plants was an iceberg lettuce with the outer appearance of a romaine (e.g., spatulate leaf shape, elongated, elliptical stature), but with all other characteristics of an iceberg (e.g., color, texture, taste and density), a dark outer color with blanched inner color, with resistance to corky root rot (from the PI 206964 parent), and resistance to lettuce mosaic virus (from the Salinas 88 parent). Those five plants were allowed to self-pollinate and the resulting $F_3$ seed collected. In 1996, the $F_3$ seed was divided into two lots. One lot was planted in a field located near the city of Santa Maria in Central California (PSR 4569) and the other in a field located near Yuma, Ariz. (PSR 4570, described below). In dividing the seed into two lots, the aim was to breed progeny from the same cross in two distinct climatic zones to select plants adapted to the two major lettuce production areas in California, summer production in Central California and winter production in Southern California and Arizona. From the resulting plants, eight single plants were selected using the same selection criteria employed for the selection of the $F_2$ plants. Those plants were allowed to self-pollinate and the resulting $F_4$ seed collected. In 1997, the $F_4$ seed was planted in a field located near the city of Santa Maria in Central California. From the resulting plants, 21 plants were selected using the same selection criteria employed for the selection of the $F_2$ and $F_3$ plants. The 21 plants were then self-pollinated and the resulting $F_5$ seed was collected. In 1998, the $F_5$ seed was planted in a field located near Santa Maria, in Central California. From the resulting plants, 25 plants were selected using the same selection criteria employed for the selection of the $F_2$, $F_3$, and $F_4$ plants. The 25 plants were then self-pollinated and the resulting $F_6$ seed was collected. In 1999, the $F_6$ seed was planted in a field located near Salinas, Central California. From the resulting plants, 44 highly uniform plants were selected using the same selection criteria employed for the selection of the $F_2$, $F_3$, $F_4$, and $F_5$ plants. The number PSR 4569 was assigned and the 44 plants were then self-pollinated and the resulting $F_7$ seed was collected. In 2000, the $F_7$ seed was bulked and trialed in growers' fields in Central California. During trials of PSR 4569 in 1999 and 2000, neither genetic variants nor off-types have been observed in more than 9,000 plants. This was an experimental trial in order to evaluate PSR 4569 in field conditions.

PSR 4569 has unique characteristics which are ideally suited for the American fresh vegetable industry. PSR 4569 has head height similar to romaine and head diameter narrower than both romaine and iceberg, due to the compact nature of its head (a crisphead characteristic) but elongated to a romaine height (Table 1). Its leaf color, internal qualities, and nutritional components all come from its crisphead background. Its exterior and interior color, head weight, leaf thickness, and tendency to flowering (number of days to 15 cm.), as well as the total composition of vitamins and minerals are all typical of crisphead. Such internal qualities contribute to the crisphead type, e.g. crisp interior leaves (leaf thickness), pale exterior and interior color, and a distinct iceberg taste (nutritional components). Potentially mistaken for a romaine cultivar, PSR 4569 is clearly a crisphead in all aspects except for its shape.

PSR 4569 is adapted to all coastal production areas of Central California. It contains the mo gene conferring resistance to lettuce mosaic virus (the mo gene was released by the USDA in 1975) and the cor gene, conferring resistance to corky root rot, strain CA1 (the cor gene was released by the Wisconsin State Experiment Station in 1978). Due to the size and shape of this cultivar, the breeding strategy required careful study and selection of this phenotype, without which the discovery of this invention would not have been possible.

PSR 4569 is a vigorous cultivar that has a healthy root system. The healthy root system is a result of the cultivar's resistance to corky root rot. All PSR 4569 plants tested for resistance to corky root rot had scores of 0 (resistant, based on rating system of 0-5, Dr. A. H. C. van Bruggen, U. C. Davis, California Lettuce Research Program, Annual Report, 1987, pp:30-41) and were clean of any lesions on the roots caused by bacterial infection. The susceptible control, cultivar Green Towers, all had scores of 4 or 5 (susceptible) and showed lesions on their roots. More specifically, PSR 4569 has a root system with high root mass. Typically, iceberg cultivars that are susceptible to corky root rot have a root system that has a low root mass. Because of this low root mass, such cultivars require frequent watering, specifically, 3 to 4 irrigations after thinning, in order to prevent them from drying out and having a small head size.

TABLE 1

*Lactuca sativa* cultivar PSR 4569 has the following morphological and other characteristics:

| | |
|---|---|
| Seed Color: | Black |
| Light Dormancy: | Not required |
| Heat Dormancy: | Susceptible |
| Shape of Cotyledons: | Spatulate |
| Leaf Shape: | Spatulate |
| Leaf Length/Width Leaf Ratio: | 1.5 |
| Leaf Margin Incision Depth: | Moderate |
| Leaf Margin Indentation: | Shallowly Dentate |
| Leaf Apical Margin Undulation: | Moderate |
| Leaf Color: | Dark Green, RHS 146A |
| Leaf Anthocyanin Distribution: | Absent |
| Leaf Glossiness: | Moderate |
| Leaf Blistering: | Absent |
| Head Formation: | Semi-open |
| Leaf Thickness: | Thick, 1.1 ± 0.2 mm |
| Plant Height: | Tall, 27.5 ± 0.9 cm |
| Head Diameter: | Medium, 17.2 ± 2.4 cm |
| Head Weight: | Heavy, 1328 ± 9.8 g |
| Tendency to Bolt: | Moderate, 66 days to 15 cm |

PSR 4569 is the subject of a PVP application in the United States (#200000266).

Example 2

Development and Characteristics of Lettuce Breeding Line PSR 4570

In 1996, the second lot of $F_3$ seed described in Example 1 was planted in a field located near Yuma, Ariz. From the resulting plants, six single plants were selected using the same selection criteria employed for the selection of the $F_2$ plants. Those plants were allowed to self-pollinate and the resulting $F_4$ seed collected. In 1997, the $F_4$ seed was planted in a field located near Yuma, Ariz. From the resulting plants, 16 plants were selected using the same selection criteria employed for the selection of the $F_2$ and $F_3$ plants. The 16 plants were then self-pollinated and the resulting $F_5$ seed was collected. In 1998, the $F_5$ seed was planted in a field located near Yuma, Ariz. From the resulting plants, 17 plants were selected using the same selection criteria employed for the selection of the $F_2$, $F_3$, and $F_4$ plants. The 17 plants were then self-pollinated and the resulting $F_6$ seed was collected. In 1999, the $F_6$ seed was planted in a field located near Yuma, Ariz. From the resulting plants, 34 highly uniform plants were selected using the same selection criteria employed for the selection of the $F_2$, $F_3$, $F_4$, and $F_5$ plants. The number PSR 4570 was assigned and the 34 plants were then self-pollinated and the resulting $F_7$ seed was collected. In 2000, the $F_7$ seed was bulked and trialed in growers' fields. During trials of PSR 4570 in 1999 and 2000, neither genetic variants nor off-types have been observed in more than 10,000 plants. This was an experimental trial in order to evaluate PSR 4570 in field conditions.

Like PSR 4569, PSR 4570 has unique characteristics which are ideally suited for the American fresh vegetable industry. PSR 4570 is similar to PSR 4569 except that PSR 4569 was selected for cultivation in production areas of Coastal California, while PSR 4570 was selected for cultivation in production areas of Southern California and Arizona. The resulting differences are two-fold. PSR 4570 is more vigorous than PSR 4569. Harvest weights for PSR 4570 average 10% higher than PSR 4569. Also, the overall size of PSR 4570 is larger and plant diameter wider than PSR 4569. The other difference is in the extent of leaf undulation. PSR 4569 has a higher degree of leaf undulation than does PSR 4570.

PSR 4570 is adapted to desert production areas of Southern California and Arizona. It contains the cor gene, conferring resistance to corky root rot, strain CA1 (the cor gene was released by the Wisconsin State Experiment Station in 1982), but does not contain the mo gene, conferring resistance to lettuce mosaic virus. Due to the size and shape of this cultivar, the breeding strategy required careful study and selection of this phenotype, without which the discovery of this invention would not have been possible.

PSR 4570 is a vigorous cultivar that has a healthy root system. The healthy root system is a result of the cultivar's resistance to corky root rot. All PSR 4570 plants tested for resistance to corky root rot had scores of 0 (resistant, using the same rating system as with PSR 4569) and were clean of any lesions on the roots caused by bacterial infection. The susceptible control, cv. Green Towers, all had scores of 4 or 5 (susceptible) and showed lesions on their roots. More specifically, PSR 4570 has a root system with high root mass. Typically, iceberg cultivars that are susceptible to corky root rot have a root system that has a low root mass. Because of this low root mass, such cultivars require frequent watering, specifically, 3 to 4 irrigations after thinning, in order to prevent them from drying out and having a small head size.

TABLE 2

*Lactuca sativa* cultivar PSR 4570 has the following morphological and other characteristics:

| | |
|---|---|
| Seed Color: | Black |
| Light Dormancy: | Not required |
| Heat Dormancy: | Susceptible |
| Shape of Cotyledons: | Spatulate |
| Leaf Shape: | Spatulate |
| Leaf Length/Width Leaf Ratio: | 1.5 |
| Leaf Margin Incision Depth: | Moderate |
| Leaf Margin Indentation: | Shallowly Dentate |
| Leaf Apical Margin Undulation: | Moderate |
| Leaf Color: | Dark Green, RHS 146A |
| Leaf Anthocyanin Distribution: | Absent |
| Leaf Glossiness: | Moderate |
| Leaf Blistering: | Absent |
| Head Formation: | Semi-open |
| Leaf Thickness: | Thick, 1.2 ± 0.2 mm |
| Plant Height: | Tall, 28.0 ± 1.2 cm |
| Head Diameter: | Medium, 20.2 ± 2.5 cm |
| Head Weight: | Heavy, 1439 ± 10.4 g |
| Tendency to Bolt: | Moderate, 61 days to 15 cm |

Example 3

Development and Characteristics of Lettuce Breeding Line PSR 6425

Breeding line PSR 6425 originated from the crosses Green Towers X Barcarole and PI 289059A X PSR 11093 in 1991. Green Towers was released by Harris Moran Co. in 1988, Barcarole is an old European romaine variety, PI289059A was obtained from the USDA's Western Regional Plant Introduction Station, Pullman, Wash., and PSR 11093 is an internal breeding line of Seminis Vegetable Seeds, Inc. In 1992, the resulting $F_1$ seed from these two crosses were collected, planted, and allowed to self-pollinate. The resulting $F_2$ seed was collected. In 1993, the $F_2$ seed was planted. From the resulting plants, 8 plants of the first cross and 9 plants of the second cross were selected. The selection criteria for the first cross was a romaine lettuce with typical characteristics (e.g., spatulate leaf shape, elongated, elliptical stature, and a semi-loose arrangement of leaves arranged in a cylindrical shape), while the selection criteria for the second cross was an iceberg lettuce with typical characteristics (e.g., spherical shape, pale green color, crisp texture, bland taste, and a firm density). The selected plants were allowed to self-pollinate and the resulting $F_3$ seed collected. In 1994, the $F_3$ seed was sown from plants of both crosses. From the resulting plants, 12 plants were selected from the first cross and 14 plants were selected from the second cross, using the same selection criteria employed for the selection of the $F_2$ plants. Those plants were allowed to self-pollinate and the resulting $F_4$ seed collected. In 1995, the $F_4$ seed was planted. From the resulting plants, six plants were selected from the first cross and 11 plants from the second cross using the same selection criteria employed for the selection of the $F_2$ and $F_3$ plants. Those plants were then self-pollinated and the resulting $F_5$ seed was collected for both crosses. In 1996, the $F_5$ seed was planted, raised to the flowering stage, and then crossed with the first cross (Green Towers X Barcarole) $F_5$ used as the female parent and the second cross (PI 289059A X PSR 11093) $F_5$ used as the male parent. From the cross, $F_1$ was planted in 1997 and allowed to self-pollinate. The resulting $F_2$ seed was collected. In 1998, the $F_2$ seed was planted. From the resulting plants, 10 plants were selected. The selection criteria for these plants was an iceberg lettuce with the outer appearance of a romaine (e.g., spatulate leaf shape, elongated, elliptical stature), but with all other characteristics of an iceberg (e.g., color, texture, taste and density), and a dark outer color with blanched inner color. Of the resulting plants, 20 plants were selected. The 20 plants were then self-pollinated and the resulting $F_3$ seed was collected. In 1999, the $F_3$ seed was planted. From the resulting plants, 15 plants were selected using the same selection criteria employed for the selection of the $F_2$ plants. In 2000, $F_4$ plants were selected using the same selection criteria employed for the selection of the $F_2$ and $F_3$ plants.

TABLE 3

*Lactuca sativa* cultivar PSR 6425 has the following morphological and other characteristics:

| | |
|---|---|
| Seed Color: | White |
| Light Dormancy: | Not required |
| Heat Dormancy: | Susceptible |
| Shape of Cotyledons: | Spatulate |
| Leaf Shape: | Spatulate |
| Leaf Length/Width Leaf Ratio: | 1.3 |
| Leaf Margin Incision Depth: | Mostly Entire |
| Leaf Margin Indentation: | Slightly Dentate |
| Leaf Apical Margin Undulation: | Moderate |
| Leaf Color: | Dark Green, RHS 146A |
| Leaf Anthocyanin Distribution: | Absent |
| Leaf Glossiness: | Moderate |
| Leaf Blistering: | Absent |
| Leaf Thickness: | Thick, 1.0 ± 0.3 mm |
| Plant Height: | Medium, 20.0 ± 1.6 cm |
| Head Diameter: | Medium, 14.0 ± 1.3 cm |
| Head Formation: | Semi-open |
| Head Weight: | Medium, 926 ± 6.9 g |
| Tendency to Bolt: | Moderate, 61 days to 15 cm |

Due to the phenotype of this cultivar, the breeding methods required specific selection of this specialized plant shape, without which the discovery of this invention would not have been possible. PSR 6425 is similar to PSR 4569 in its overall shape and appearance, however it has a smaller head (60% as tall and 50% as heavy as PSR 4569), and its head is more exposed on top. Leaf margins are nearly smooth, compared to a slight undulation for PSR 4569, while leaf color is similar. Like PSR 4569, PSR 6425 is adapted to the production areas of California and Arizona.

Example 4

Development and Characteristics of Lettuce Breeding Line PSR 6595

Breeding line PSR 6595 originated from the crosses Augustus X El Dorado and Moraleja X Clemente in 1991. Cultivars Augustus, El Dorado, Moraleja, and Clemente are all varieties sold by Seminis Vegetable Seeds, Inc. In 1992, the resulting $F_1$ seed from these two crosses were collected, planted, and allowed to self-pollinate. The resulting $F_2$ seed was collected. In 1993, the $F_2$ seed was planted. From the resulting plants, three plants of the first cross and 11 plants of the second cross were selected. The selection criteria for the first cross were an iceberg lettuce with typical characteristics (e.g., spherical shape, pale green color, crisp texture, bland taste, and a firm density), while the selection criteria for the second cross was a romaine lettuce with typical characteristics (e.g., spatulate leaf shape, elongated, elliptical stature, and a semi-loose arrangement of leaves arranged in a cylindrical shape). The selected plants were allowed to self-pollinate and the resulting $F_3$ seed collected. In 1994, the $F_3$ seed was sown from plants of both crosses, raised to the flowering stage, and then crossed with the first cross (Augustus X El Dorado) $F_3$ used as the female parent and the second cross (Moraleja X Clemente) $F_3$ used as the male parent. From the cross, $F_1$ seed was planted in 1995 and allowed to self-pollinate. The resulting $F_2$ seed was collected. In 1996, the $F_2$ seed was planted. From the resulting plants, seven plants were selected. The selection criteria for these plants was an iceberg lettuce with the outer appearance of a romaine (e.g., spatulate leaf shape, elongated, elliptical stature), but with all other characteristics of an iceberg (e.g., color, texture, taste and density), and a dark outer color with blanched inner color. Of the resulting plants, 10 plants were selected. The 10 plants were then self-pollinated and the resulting $F_3$ seed was collected. In 1997, the $F_3$ seed was planted. From the resulting plants, six plants were selected using the same selection criteria employed for the selection of the $F_2$ plants. In 1998 $F_4$ plants were selected using the same selection criteria employed for the selection of the $F_2$ and $F_3$ plants. From the resulting plants, 16 plants were selected and self-pollinated and the resulting $F_5$ seed was sown in 1999. Of the resulting plants, 10 plants were selected and allowed to self-pollinate resulting in $F_6$ seed.

TABLE 4

*Lactuca sativa* cultivar PSR 6595 has the following morphological and other characteristics:

| | |
|---|---|
| Seed Color: | White |
| Light Dormancy: | Not required |
| Heat Dormancy: | Susceptible |
| Shape of Cotyledons: | Spatulate |
| Leaf Shape: | Spatulate |
| Leaf Length/Width Leaf Ratio: | 2.1 |
| Leaf Margin Incision Depth: | Deep |
| Leaf Margin Indentation: | Coarsely Dentate |

TABLE 4-continued

Lactuca sativa cultivar PSR 6595 has the
following morphological and other characteristics:

| | |
|---|---|
| Leaf Apical Margin Undulation: | Slight |
| Leaf Color: | Dark Green, RHS 146A |
| Leaf Anthocyanin Distribution: | Absent |
| Leaf Glossiness: | Moderate |
| Leaf Blistering: | Slight |
| Head Formation: | Semi-open |
| Leaf Thickness: | Medium, 0.9 ± 0.2 mm |
| Plant Height: | Medium, 19.6 ± 0.8 cm |
| Head Diameter: | Medium, 14.1 ± 2.3 cm |
| Head Weight: | Medium, 914 ± 9.9 g |
| Tendency to Bolt: | Moderate, 61 days to 15 cm |

Because of the special phenotype, the breeding needed to select the size and shape were specific to this cultivar. This unique plant design would not have been noticed, if the detailed selection criteria were not applied. PSR 6595 is also similar to PSR 4569 in its overall shape and appearance, however it has a less compact head and a looser arrangement of leaves around its head. PSR 6595 is 80% as tall and 60% as heavy as PSR 4569, and the head is also more exposed on top. Leaf margins are similar to PSR 4569, but leaf color is darker. Like PSR 4569, PSR 6595 is adapted to the production areas of California and Arizona. Its disease resistance levels are unknown at this time.

Example 5

Development and Characteristics of Lettuce Breeding Line PSR 6032

In 1995 the leaf lettuce variety PSR 0156 was crossed as the female parent with the crisphead lettuce cultivar Tiber as the male parent using traditional cross hybridization techniques. PSR 0156 is a leaf lettuce known to be a source of resistance to lettuce mosaic virus resistance and is an internal breeding line of Seminis Vegetable Seeds, Inc. Cultivar Tiber is a public variety released by the USDA in 1995; it is a crisphead lettuce known to be a source of resistance to lettuce mosaic virus and was obtained from the United States Department of Agriculture, ARS, 1636 East Alisal Street, Salinas, Calif. 93905. In 1996, the resulting $F_1$ seed from the cross was collected, planted, and allowed to self-pollinate. The resulting $F_2$ seed was collected. In 1997, the $F_2$ seed was planted. From the resulting plants, three plants were selected. The selection criteria for these plants was an iceberg lettuce with the outer appearance of a romaine (e.g., spatulate leaf shape, elongated, elliptical stature), but with all other characteristics of an iceberg (e.g., color, texture, taste and density), a dark outer color with blanched inner color, with resistance to lettuce mosaic virus (from the PSR 0156 and the Tiber parent). Those three plants were allowed to self-pollinate and the resulting $F_3$ seed collected. In 1998, the $F_3$ seed was planted. From the resulting plants, five single plants were selected using the same selection criteria employed for the selection of the $F_2$ plants. Those plants were allowed to self-pollinate and the resulting $F_4$ seed collected. In 1999, the $F_4$ seed was planted. From the resulting plants, 11 plants were selected using the same selection criteria employed for the selection of the $F_2$ and $F_3$ plants. The 11 plants were then self-pollinated and the resulting $F_5$ seed was collected. In 2000, the $F_5$ seed was planted. From the resulting plants, 10 plants were selected using the same selection criteria employed for the selection of the $F_2$, $F_3$, and $F_4$ plants. The 10 plants were then self-pollinated and the resulting $F_6$ seed was collected. In 2001, the $F_6$ seed was planted. From the resulting plants, 19 highly uniform plants were selected using the same selection criteria employed for the selection of the $F_2$, $F_3$, $F_4$, and $F_5$ plants.

TABLE 5

Lactuca sativa cultivar PSR 6032 has the
following morpholical and other characteristics:

| | |
|---|---|
| Seed Color: | Black |
| Light Dormancy: | Not required |
| Heat Dormancy: | Susceptible |
| Shape of Cotyledons: | Spatulate |
| Leaf Shape: | Spatulate |
| Leaf Length/Width Leaf Ratio: | 2.0 |
| Leaf Margin Incision Depth: | Shallow |
| Leaf Margin Indentation: | Moderately Dentate |
| Leaf Apical Margin Undulation: | Moderate |
| Leaf Color: | Dark Green, RHS 146A |
| Leaf Anthocyanin Distribution: | Absent |
| Leaf Glossiness: | Moderate |
| Leaf Blistering: | Slight |
| Head Formation: | Semi-open |
| Leaf Thickness: | Medium, 0.9 ± 0.2 mm |
| Plant Height: | Slightly Tall, 24.8 ± 1.2 cm |
| Head Diameter: | Medium, 16.1 ± 2.5 cm |
| Head Weight: | Heavy, 1239 ± 10.1 g |
| Tendency to Bolt: | Moderate, 61 days to 15 cm |

Due to the size and shape of this cultivar, the breeding strategy required careful study and selection of this phenotype, without which the discovery of this invention would not have been possible. PSR 6032 is also similar to PSR 4569 in its overall shape and appearance, however its head remains more open at maturity and its leaf margins have a much higher degree of undulation. PSR 6595 is as tall as PSR 4569 and 70% as heavy with a high concentration of tightly crowded leaves at the opening on top. Leaf color is also similar to that of PSR 4569, and like PSR 4569, PSR 6032 is adapted to the production areas of California and Arizona.

Example 6

Corky Root Inoculation Techniques

Using soil samples, the organism causing corky root can be isolated by using 2-3 week old seedling of a susceptible variety, like "Salinas," as baits. Soil suspensions are made by using 50 g of soil in 75 ml of distilled water plus 3 drops of Tween.™ The suspensions are stirred for 10-20 minutes and filtered through six layers of cheesecloth. Suspension (5 ml) is dispensed at the base of each of the five 2-3 week old seedlings in a greenhouse. Three-four weeks after inoculation, the plants are uprooted and the bacteria is isolated from the yellow or corked areas on the roots.

Root samples are rinsed under running tap water, sonicated in 20 ml of sterile water, and comminuted in a sterile mortar with 10 ml of sterile distilled water. The cell suspensions obtained from the root surface by sonication and from comminuted roots are filtered through a 65 micron filter and 0.04 ml of filtered suspension (undiluted and 10-fold diluted) is spread into plates of S-medium amended with streptomycin sulfate. The plates are incubated at 28° Celsius for 10 days. The slow-growing colonies are identified by their translucent, later opaque colonies in S-medium.

Bacterial cultures are stored long term at −85° Celsius. A 72-hour liquid culture in S-medium is diluted to 15% glycerol. The cultures are slightly unstable after successive transfers on solid S-medium and pathogenicity may be affected.

To increase the inoculum for screening, one cryovial is thawed and added to 10 ml liquid S-medium. The medium is left at room temperature with continual shaking for 4 days. *R. suberifaciens* is not a vigorous growing bacteria. If growth is heavy after 2 days, then there is a strong likelihood of contamination. The original 10 ml is used to seed larger volumes of liquid S-medium at the rate of 1 ml:1 liter. To check for contaminants, streak 1 loop onto a plate of S-medium and CS-20. *R. suberifaciens* does not grow well on CS-20. After 3-4 days at room temperature, there will be distinct colonies on S-medium. After 5-6 days of continual agitation/shaking at room temperature, the cultures will be cloudy and turbid. The cultures are then diluted 50% with deionized, distilled water.

The diluted culture media is applied to 1020 trays of 7-day old seedlings at a rate of at least 500 ml per tray. Any excess water in the trays is removed prior to inoculation by sifting in the tray before adding inoculum.

Resistant varieties of lettuce are available and include commonly available varieties such as "Greenlake, Montello, Southbay, Raleigh, Misty Day, and Glacier." Susceptible varieties are also commonly available and include "Salinas."

The screening of lettuce seedlings conveniently takes place in K36D1 cell inserts in a 1020 tray without holes. The tray combinations are available from Kord Products, Ltd. Bramaton, Ontario, Canada. 10-20 seeds are sown per cell in vermiculite. The seedlings are kept at 17-28° Celsius throughout the test with 14 hours of light. The trays are misted daily for at least 2 weeks and/or watered from below by adding about 1 cm of water to the tray. Between waterings, the tray is allowed to become dry, yet the vermiculite should remain moist.

Approximately 10 days after sowing, the flats are flooded with half strength Hoaglands solution to supply nutrition. The seedlings are watered every other week with 0.005M $CA(NO_3)_2 + 0.005$ $KNO_3$.

The seedlings are inoculated with the bacteria approximately 7-8 days after sowing. The preferred time is when the root system has started to expand. The liquid in the bottom of the tray is removed and inoculum is added to a depth of 1 cm. The seedlings are not watered for at least 24 hours. The trays may be misted. A second inoculation is done 2 weeks later.

Post inoculation, the seedlings are maintained as they were during the growth phase. The flats are kept moist with a maximum of 1 cm of water in the tray. The trays may be allowed to go dry; however, the vermiculite must remain wet at all times.

Susceptibility to corky root is presented by plant stunting and poorly developed root systems. The tap root develops yellow to golden oblong lesions, especially where the lateral root has emerged. The entire root system is brown to golden and, in advanced cases, the tap root is corky and brown. The absence of stunting, and lesions under the conditions provided is evidence of resistance. The duration of test from sowing to reading is approximately 4 weeks.

Suitable techniques are described in Van Bruggen et al. 1990, Host Range of *Rhizomas suberifaciens*, the Causal Agent of Corky Root of Lettuce, Plant Disease. 74(8):581-584; Van Bruggen et al. 1990, The Effect of Cover Crops and Fertilization with Ammonium Nitrate of Corky Root of Lettuce, Plant Disease 74(8):584-589; and Van Bruggen et al. 1990, Distinction Between Infectious and Non-infectious Corky Root of Lettuce in Relation to Nitrogen Fertilizer, J. Amer. Soc. Hort. Sci. 115(5):762-770.

Example 7

Screening for Lettuce Mosaic Virus

Resistance to Lettuce Mosaic Virus (LMV) is determined using a standard, mechanical inoculation. Three to four weeks prior to inoculation of test plants or breeding lines, the virus is increased by inoculation on susceptible lettuce varieties like Green Towers, Salinas or Vanguard. Resistance checks can be done using varieties Don Juan, Salinas 88 and Vanguard 75. The infected leaves are then ground in a buffer solution of 0.5M potassium phosphate ($K_2HPO_4$, 8.71 g/l) at pH 7.2 in a ratio of 1 g leaf to 4 ml buffer solution. An antioxidant (mercaptoethanol) is also added, as well as activated charcoal at 0.25 g. Carborundum at 0.4 g can be added to the inoculum, then rubbed on the leaves of the test plants.

The test plants include both seedlings and mature plants. They are transplanted in flats until they recover to their 3-4 leaf stage, when they are inoculated.

About 3 weeks after inoculation, plants showing symptoms are culled out, and the remaining plants grown until the flag leaf stage, when they are rated again for mottling symptoms.

Suitable references include: Pink, D. A., et al. 1992 "Differentiation of Pathotypes of Lettuce Mosaic Virus," Plant Pathology, 41:5-12; and Ryder, E. J., 1973, "Seed Transmission of Lettuce Mosaic Virus in Mosaic Resistant Lettuce," J. Amer. Soc. Hort. Sci., 98(6):610-614.

DEPOSIT INFORMATION

Lettuce, *Lactuca sativa* L., seeds of PSR 4569 have been placed on deposit with the American Type Culture Collection (ATCC), Manassas, Virginia, under Deposit Accession Number PTA-3249 on Mar. 28, 2001.

Lettuce, *Lactuca sativa* L., seeds of PSR 4570 have been placed on deposit with the American Type Culture Collection (ATCC), Manassas, Virginia, under Deposit Accession Number PTA-3247 on Mar. 28, 2001.

Lettuce, *Lactuca sativa* L., seeds of PSR 6425; PSR 6595 and PSR 6032 have been placed on deposit with the American Type Culture Collection (ATCC), Manassas, Va., under Deposit Accession Number PTA-3248 on Mar. 28, 2001.

Although the foregoing invention has been described in some detail by way of illustration and example for purposes of clarity and understanding, it will be obvious that certain changes and modifications such as single gene modifications and mutations, somoclonal variants, variant individuals selected from large populations of the plants of the instant inbred and the like may be practiced within the scope of the invention, as limited only by the scope of the appended claims.

I claim:

1. A lettuce seed capable of producing a lettuce plant, said lettuce plant comprising a head having an outer leaf comprising a leaf length to width ratio between about 1.2 and about 2.7 and at least one morphological characteristic of an iceberg lettuce type selected from the group consisting of crisp texture, bland taste, high water content, and firm density.

2. The lettuce seed capable of producing the lettuce plant of claim 1, wherein said lettuce plant further comprises at least one morphological characteristic selected from the group consisting of an elliptical leaf stature, a spatulate leaf shape, and a semi open head formation.

3. The lettuce seed capable of producing the lettuce plant of claim 2, wherein said lettuce plant comprises at least two of said morphological characteristics.

4. The lettuce seed capable of producing the lettuce plant of claim 1, wherein said lettuce plant further comprises a head weight of at least 900 grams.

5. The lettuce seed capable of producing the lettuce plant of claim 1, wherein said lettuce plant further comprises a plant height of at least 19 centimeters.

6. The lettuce seed capable of producing the lettuce plant of claim 1, wherein said lettuce plant further comprises a head diameter of at least 14 centimeters.

7. The lettuce seed capable of producing the lettuce plant of claim 1, wherein said leaf length to width ratio is between about 1.2 and about 2.1.

8. The lettuce seed capable of producing the lettuce plant of claim 1, wherein said leaf length to width ratio is between about 1.2 and about 1.8.

9. The lettuce seed capable of producing the lettuce plant of claim 1, wherein the adaxial leaf blade of an inner leaf from said lettuce plant further comprises a blanched color, ranging from about RHS 145C to about RHS 145D.

10. The lettuce seed capable of producing the lettuce plant of claim 1, wherein the adaxial leaf blade of an outer leaf from said lettuce plant further comprises a color which ranges from about RHS 146A to about RHS 146B.

11. A lettuce seed capable of producing a lettuce plant, said lettuce plant comprising a head having an outer leaf comprising a leaf length to width ratio between about 1.2 and about 2.7 and taste, texture, and density of an iceberg lettuce type.

12. The lettuce seed capable of producing the lettuce plant of claim 11, wherein said lettuce plant further comprises at least one morphological characteristic selected from the group consisting of an elliptical leaf stature, a spatulate leaf shape, and a semi open head formation.

13. The lettuce seed capable of producing the lettuce plant of claim 12, wherein said lettuce plant comprises at least two of said morphological characteristics.

14. The lettuce seed capable of producing the lettuce plant of claim 11, wherein said lettuce plant comprises a head weight of at least 900 grams.

15. The lettuce seed capable of producing the lettuce plant of claim 11, wherein said lettuce plant further comprises a plant height of at least 19 centimeters.

16. The lettuce seed capable of producing the lettuce plant of claim 11, wherein said lettuce plant further comprises a head diameter of at least 14 centimeters.

17. The lettuce seed capable of producing the lettuce plant of claim 11, wherein said 1 leaf length to width ratio is between about 1.2 and about 2.1.

18. The lettuce seed capable of producing the lettuce plant of claim 11, wherein said leaf length to width ratio is between about 1.2 and about 1.8.

19. The lettuce seed capable of producing the lettuce plant of claim 11, wherein the adaxial leaf blade of an inner leaf from said lettuce plant further comprises a blanched color, ranging from about RHS 145C to about RHS 145D.

20. The lettuce seed capable of producing the lettuce plant of claim 11, wherein the adaxial leaf blade of an outer leaf from said lettuce plant further comprises a color which ranges from about RHS 146A to about RHS 146B.

21. A lettuce seed capable of producing a lettuce plant, said lettuce plant comprising at least one morphological characteristic of a romaine lettuce type selected from the group consisting of an elliptical stature, a spatulate leaf shape, and a semi open head formation and at least one morphological characteristic of an iceberg lettuce type selected from the group consisting of crisp texture, bland taste, high water content, and firm density.

22. The lettuce seed capable of producing the lettuce plant of claim 21, wherein said leaf further comprises at least two morphological characteristics of an iceberg lettuce type.

23. The lettuce seed capable of producing the lettuce plant of claim 22, wherein said lettuce plant comprises at least three of said morphological characteristics of an iceberg lettuce type.

24. The lettuce seed capable of producing the lettuce plant of claim 21, wherein said lettuce plant further comprises a head weight of at least 900 grams.

25. The lettuce seed capable of producing the lettuce plant of claim 21, wherein said lettuce plant further comprises a plant height of at least 19 centimeters.

26. The lettuce seed capable of producing the lettuce plant of claim 21, wherein said lettuce plant further comprises a head diameter of at least 14 centimeters.

27. The lettuce seed capable of producing the lettuce plant of claim 21, wherein said leaf length to width ratio is between about 1.2 and about 2.7.

28. The lettuce seed capable of producing the lettuce plant of claim 21, wherein said leaf length to width ratio is between about 1.2 and about 1.8.

29. The lettuce seed capable of producing the lettuce plant of claim 21, wherein the adaxial leaf blade of an inner leaf from said lettuce plant further comprises a blanched color, ranging from about RHS 145C to about RHS 145D.

30. The lettuce seed capable of producing the lettuce plant of claim 21, wherein the adaxial leaf blade of an outer leaf from said lettuce plant further comprises a color which ranges from about RHS 146A to about RHS 146B.

* * * * *